US010608238B2

(12) United States Patent
Mano et al.

(10) Patent No.: US 10,608,238 B2
(45) Date of Patent: Mar. 31, 2020

(54) METHOD FOR MANUFACTURING A MINIATURIZED ELECTROCHEMICAL CELL AND A MINIATURIZED ELECTROCHEMICAL CELL

(71) Applicants: CENTRE NATIONAL DE LA RECHERCHE SCIENTIFIQUE, Paris (FR); UNIVERSITE DE BORDEAUX, Bordeaux (FR); INSTITUT POLYTECHNIQUE BORDEAUX, Talence (FR)

(72) Inventors: Nicolas Mano, Talence (FR); Stephane Reculusa, Pessac (FR); Serge Ravaine, Cestas (FR); Aleksandar Karajic, Pessac (FR); Alexander Kuhn, Guillac (FR)

(73) Assignees: CENTRE NATIONAL DE LA RECHERCHE SCIENTIFIQUE, Paris (FR); UNIVERSITE DE BORDEAUX, Bordeaux (FR); INSTITUT POLYTECHNIQUE BORDEAUX, Talence (FR)

( * ) Notice: Subject to any disclaimer, the term of this patent is extended or adjusted under 35 U.S.C. 154(b) by 132 days.

(21) Appl. No.: 15/741,845

(22) PCT Filed: Jun. 29, 2016

(86) PCT No.: PCT/IB2016/053868
§ 371 (c)(1),
(2) Date: Jan. 4, 2018

(87) PCT Pub. No.: WO2017/013506
PCT Pub. Date: Jan. 26, 2017

(65) Prior Publication Data
US 2018/0205070 A1    Jul. 19, 2018

(30) Foreign Application Priority Data
Jul. 20, 2015   (EP) ................................... 15306180

(51) Int. Cl.
*H01M 4/04*       (2006.01)
*H01M 4/38*       (2006.01)
(Continued)

(52) U.S. Cl.
CPC .......... *H01M 4/0452* (2013.01); *C25D 1/006* (2013.01); *C25D 1/02* (2013.01); *C25D 1/08* (2013.01);
(Continued)

(58) Field of Classification Search
CPC ............ A61B 5/686; A61B 2560/0214; C25D 1/006; C25D 1/02; C25D 1/08;
(Continued)

(56) References Cited

U.S. PATENT DOCUMENTS

2006/0186761 A1   8/2006  Trolier-McKinstry et al.
2011/0076565 A1*  3/2011  Cho ..................... H01M 4/0473
                                                                429/231.8
(Continued)

FOREIGN PATENT DOCUMENTS

CN      104409683 A     3/2015
WO      2005/055265 A2  6/2005
WO      2010/124258 A2  10/2010

OTHER PUBLICATIONS

International Search Report dated Sep. 21, 2016, in PCT/IB2016/053868 filed Jun. 29, 2016.
(Continued)

*Primary Examiner* — Louis J Rufo
(74) *Attorney, Agent, or Firm* — Oblon, McClelland, Maier & Neustadt, L.L.P.

(57) ABSTRACT

A miniaturized electrochemical cell and a method for making it are provided. The method includes preparing at least one inner electrode of an electron conducting or semi-conducting material M1; providing a hollow support made
(Continued)

Figure 1:
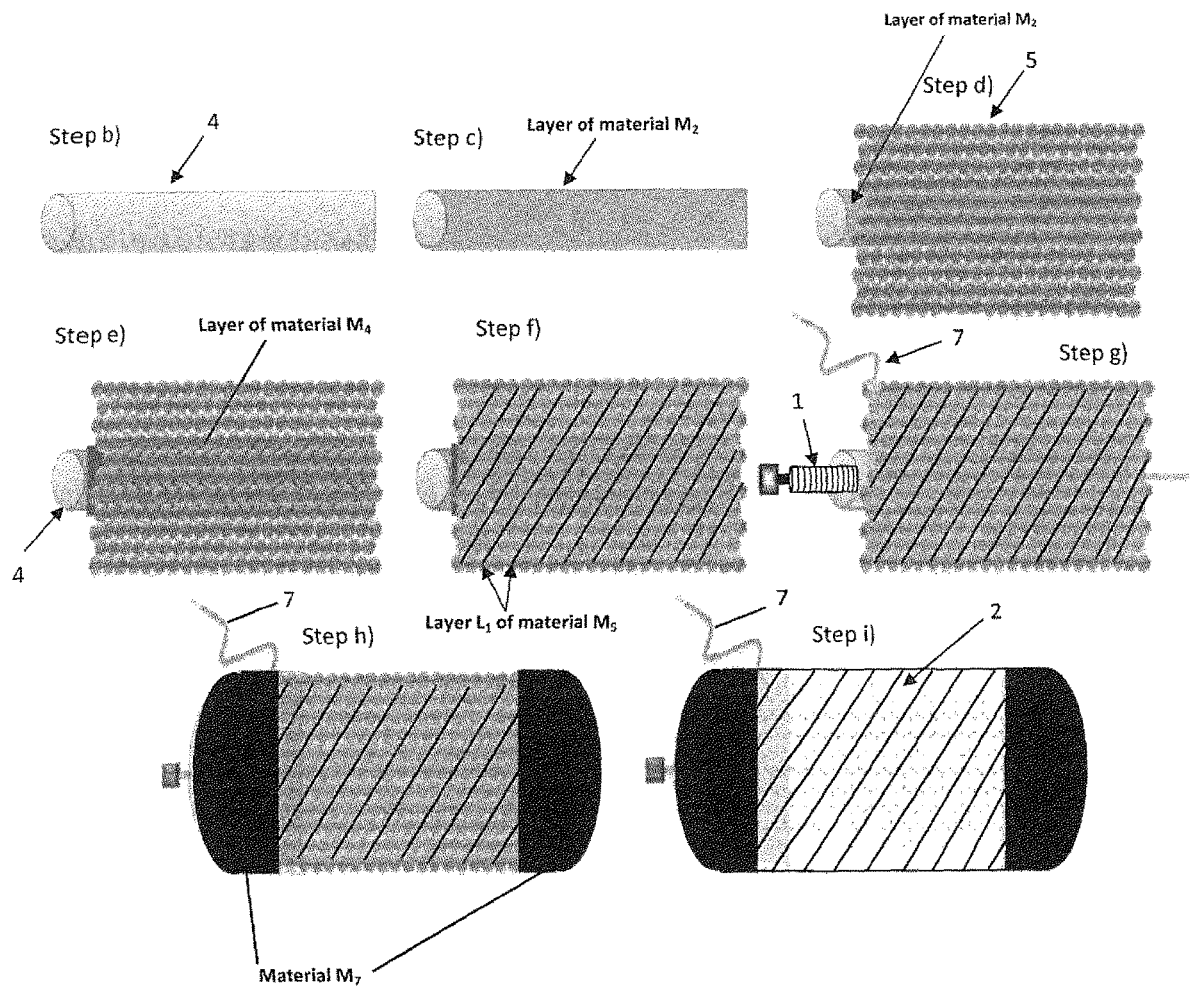

of an electrically insulating material M6 and having at least one internal hollow channel; depositing on the external surface of the support a layer of an electrically conducting material M2; forming a template of colloidal particles of an electrically insulating material M3, on the M2 layer; depositing a layer of an electrically conducting material M4 on the M2 layer; depositing a layer L1 of an electron conducting or semi-conducting material M5 on the M4 layer, introducing the at least one inner electrode into the at least one internal hollow channel of the obtained structure; stabilizing the structure at its two open ends with an electrically insulating material M7; and removing M2, M3, M4 and M6 materials.

13 Claims, 4 Drawing Sheets

(51) Int. Cl.
| | | |
|---|---|---|
| *H01M 4/76* | (2006.01) | |
| *H01M 10/04* | (2006.01) | |
| *H01M 10/38* | (2006.01) | |
| *H01M 4/1395* | (2010.01) | |
| *C25D 1/00* | (2006.01) | |
| *C25D 1/02* | (2006.01) | |
| *C25D 1/08* | (2006.01) | |
| *C25D 3/12* | (2006.01) | |
| *C25D 3/46* | (2006.01) | |
| *C25D 3/48* | (2006.01) | |
| *C25D 5/12* | (2006.01) | |
| *C25D 7/06* | (2006.01) | |
| *H01M 4/12* | (2006.01) | |
| *H01M 4/66* | (2006.01) | |
| *H01M 4/86* | (2006.01) | |
| *H01M 4/88* | (2006.01) | |
| *H01M 4/90* | (2006.01) | |
| *H01M 6/02* | (2006.01) | |
| *H01M 8/16* | (2006.01) | |
| *H01M 4/02* | (2006.01) | |
| *A61B 5/00* | (2006.01) | |

(52) U.S. Cl.
CPC ............... *C25D 3/12* (2013.01); *C25D 3/46* (2013.01); *C25D 3/48* (2013.01); *C25D 5/12* (2013.01); *C25D 7/0607* (2013.01); *H01M 4/0402* (2013.01); *H01M 4/12* (2013.01); *H01M 4/1395* (2013.01); *H01M 4/38* (2013.01); *H01M 4/661* (2013.01); *H01M 4/765* (2013.01); *H01M 4/8626* (2013.01); *H01M 4/8853* (2013.01); *H01M 4/9041* (2013.01); *H01M 6/02* (2013.01); *H01M 8/16* (2013.01); *H01M 10/0436* (2013.01); *H01M 10/38* (2013.01); *A61B 5/686* (2013.01); *A61B 2560/0214* (2013.01); *H01M 2004/021* (2013.01); *H01M 2004/025* (2013.01); *H01M 2010/0495* (2013.01); *H01M 2250/30* (2013.01); *Y02B 90/18* (2013.01)

(58) Field of Classification Search
CPC ... C25D 3/12; C25D 3/46; C25D 3/48; C25D 5/12; C25D 7/0607; H01M 4/0402; H01M 4/0452; H01M 4/12; H01M 4/1395; H01M 4/38; H01M 4/661; H01M 4/765; H01M 4/8626; H01M 4/8853; H01M 4/9041; H01M 6/02; H01M 8/16; H01M 10/0436; H01M 10/38; H01M 2010/0495; H01M 2250/30; Y02B 90/18
See application file for complete search history.

(56) References Cited

U.S. PATENT DOCUMENTS

| | | | |
|---|---|---|---|
| 2012/0009325 A1* | 1/2012 | Storment | A61F 2/91 427/2.25 |
| 2012/0034410 A1 | 2/2012 | Baumgart et al. | |
| 2012/0080313 A1 | 4/2012 | Baumgart et al. | |
| 2015/0136733 A1 | 5/2015 | Baumgart et al. | |
| 2016/0013340 A1* | 1/2016 | Mirkin | C25D 1/04 257/21 |

OTHER PUBLICATIONS

Aleksander Karajic et al., "Bottom-up Generation of Miniaturized Coaxial Double Electrodes with Tunable Porosity", Advanced Materials Interfaces, vol. 2, No. 12, Jul. 6, 2015, XP002751090, 6 pages.

* cited by examiner

METHOD FOR MANUFACTURING A MINIATURIZED ELECTROCHEMICAL CELL AND A MINIATURIZED ELECTROCHEMICAL CELL

The invention relates to a method for manufacturing a miniaturized electrochemical cell and to a miniaturized electrochemical cell.

In miniaturized electrochemical systems the overall dimensions of a device depend on the size of the single components. For example, in batteries, generally a steel case is used to prevent corrosive or toxic components, such as electrolyte, etc. . . . from leaking, dominating the size and limiting efficient miniaturization of the device. Another example is implantable biofuel cells, which may deliver the electrical power for small medical devices (e.g. glucose sensors) permanently remaining in the body. The subcutaneous interstitial fluid here serves as the electrolyte and thus no case is required. But in order to drive the electrochemical reaction, at least two independent electrodes, serving as the anode and the cathode, still need to be available. The integration of independently addressable electrodes in a single device would offer great potential for a further miniaturization of electrochemical cells, especially in fuel cells or batteries.

EP application 14306341.0 discloses a method for manufacturing a miniaturized electrochemical cell composed of two independent macroporous electrodes with a tunable inter-electrode spacing.

In the method of EP application 14306341.0, a single colloidal template is used for manufacturing a miniaturized electrochemical cell consisting of electrodes with a high surface area, i.e. macroporous electrodes.

However, with this method, the distance between two electrodes is at the maximum of 100 µm. Indeed, obtaining an inter-electrode distance larger than 100 µm would require the use of hundreds of colloidal particles layers. Furthermore, both electrodes (the inner and the outer) are made of a macroporous material.

The invention aims at proposing a method for manufacturing a miniaturized electrochemical cell, this method being time-saving and more efficient, and enabling to extend the ranges of the inter-electrode distances and therefore the volume of solution that can be stored in-between. The method of the invention also enables to use an inner electrode made of a material which can be macroporous or not.

For this aim, the invention proposes a method for manufacturing a miniaturized electrode cell consisting of coaxial electrodes, the method comprising the following steps:
a) preparing at least one inner electrode made of an electron conducting or semi-conducting material $M_1$,
b) providing a sacrificial hollow support made of an electrically insulating material $M_6$, this support having at least one internal channel, the dimensions of this at least one internal channel being higher than the external dimensions of the inner electrode and the thickness of the walls of this support being at least equal to the width of the gap which is desired between the electrodes,
c) depositing on the external surface of this support a sacrificial layer of an electrically conducting material $M_2$, by an electroless deposition method,
d) forming a sacrificial template of colloidal particles made of an electrically insulating material $M_3$, on the layer of electrically conducting material $M_2$ deposited in step c),
e) depositing a sacrificial layer of an electrically conducting material $M_4$ on the layer of electrically conducting material $M_2$, through the template by an electro-deposition method,
f) depositing a layer $L_1$ of an electron conducting or semi-conducting material $M_5$ on the layer of electrically conducting material $M_4$ by an electro-deposition method, through the template, this layer $L_1$ having a thickness equal to the thickness of the outer electrode to be obtained,
g) introducing the at least one inner electrode into the at least one internal channel of the structure obtained in step f),
h) stabilizing the structure obtained in step g) at its two open ends with an electrically insulating material $M_7$ which is not soluble in a solvent in which the materials $M_2$, $M_3$, $M_4$, and $M_6$ are soluble,
i) removing the materials $M_2$, $M_3$, $M_4$ and $M_6$, and
optionally repeating steps b) to g) at least one time, the structure obtained after each step g) constituting the inner electrode to be introduced in the at least one internal channel of each structure obtained in step f).

In this method, preferably the electron conducting or semi-conducting material $M_1$ of the at least one inner electrode is macroporous and step a) preferably comprises the following steps:
a1) providing a substrate $S_1$ having the shape wanted for the inner electrode and made of an electron conducting or semi-conducting material $M_8$,
a2) forming a sacrificial template $T_1$ of colloidal particles made of an electrically insulating material $M_9$ which is soluble in a solvent in which the material $M_7$ is not soluble,
a3) depositing a layer $L_1$ of an electron conducting or semi-conducting material $M_1$ on the surface of the substrate $S_1$, through the colloidal particles of the template $T_1$ by an electro-deposition method, the substrate $S_1$ coated with the layer $L_1$ having the shape and the external dimensions wanted for the inner electrode,
a4) removing the material $M_9$ with a solvent in which the materials $M_1$, $M_7$ and $M_8$ are not soluble.

Preferably, the materials $M_1$, $M_5$ and $M_8$ are, independently from each other, chosen among Pd, Ag, Cr, Au, Pt, Cu, Ni, Zn, polypyrrole (PPy), polyaniline (PAni), polyacetylene, poly(3,4-ethylenedioxythiophene:sodium poly (styrene sulfonate) (PEDOT:PSS), preferably the materials $M_1$, $M_5$ and $M_8$ are Au.

Also preferably, the materials $M_6$, $M_3$ and $M_9$ are independently from each other, chosen among $SiO_2$, a glass or a plastic which is preferably polystyrene.

Still preferably, the materials $M_2$ and $M_4$ are independently from each other chosen among Ag, Ni, Au, Cu.

More preferably the material $M_2$ is Ag and the material $M_4$ is Ni.

In the method of the invention, step a) can be carried out after step f).

Step h) can be a step of stabilizing the two ends of the structure obtained in step g) with an epoxy resin or a silicon based adhesive which is then hardened or reticulated.

Preferably, the materials $M_3$, $M_6$ and $M_9$ are $SiO_2$, the material $M_2$ is Ag, and the material $M_4$ is Ni, and step i) comprises a step i1) of dissolving the materials $M_3$, $M_6$ and $M_9$ with a solution of hydrofluoric acid, and a step i2) of dissolving the materials $M_2$ and $M_4$ with a solution of nitric acid or sulfuric acid.

In a first embodiment of the method of the invention, the support and the substrate $S_1$ are cylinders.

In a second embodiment of the method of the invention, the support and the substrate $S_1$ are parallelepipeds with a square or rectangular section.

The invention also proposes a miniaturized electrochemical cell consisting of:
from 2 to 10, preferentially from 2 to 5, coaxial electrodes having a thickness of from 1 to 50 μm made of identical or different conducting or semi-conducting material $M_1$ and macroporous material $M_5$, the inter-distance between each electrode being higher than 100 m, and an addressing wire (7).

The materials $M_1$ and $M_5$ are, independently from each other, chosen among Pd, Ag, Cr, Au, Pt, Cu, Ni, Zn, polypyrrole (PPy), polyaniline (PAni), polyacetylene, poly (3,4-ethylenedioxythiophene:sodium poly(styrene sulfonate) (PEDOT:PSS). Preferably the materials $M_1$ and $M_5$ are Au.

In a first embodiment, the electrodes have a cylinder shape.

In a second embodiment, the electrodes have a parallelepiped shape.

In the invention, the followings terms have the following meanings:
"colloidal template" means a stack of colloidal particles which are made of an electrically insulating material,
"colloidal particles" designates particles having their largest dimension comprised between 20 to 2 000 nm, preferably of from 100 to 1 200 nm,
"spherical particles" means particles having in all points the same diameter or having a difference between the largest diameter and the smallest diameter of less than 10%,
"potentiostatic deposition" or "electro-deposition" means an electrochemical deposition at a constant potential,
"single channel support" means a hollow cylinder or parallelepiped having one internal cavity,
"multi-channel support" means a cylinder or parallelepiped having more than one hollow internal cavity, each cavity extending along the length of the cylinder or parallelepiped,
"macroporous material" means a material having open and closed pores, these pores having their largest dimension comprised between 20 to 2000 nm, preferably comprised between 100 and 1200 nm.
"sacrificial layer" means a layer which is intended to be not present in the final electrode,
"sacrificial template" means a template which is intended to be not present in the final electrode, The following materials are used for manufacturing the outer electrode which is used in the invention:
"material $M_6$" designates an electrically insulating material constituting a support for manufacturing the outer electrode used in the invention,
"material $M_2$" designates an electrically conducting material constituting a first layer deposited on the support made of the material $M_6$,
"material $M_3$" designates an electrically insulating material constituting the colloidal particles of a template deposited on the first layer of material $M_2$,
"material $M_4$" designates an electrically conducting material, different from material $M_2$, and constituting a second layer deposited on the first layer of material $M_2$, through the template of colloidal particles made of material $M_3$,
material $M_5$ designates an electron conducting or semi-conducting material constituting the outer electrode.

The following materials are used in connection with the inner electrode used in this invention:
"material $M_1$" designates an electron conducting or semi-conducting material from which the inner electrode is made,
material $M_8$" designates an electron conducting or semi conducting material which constitutes a substrate used for manufacturing an inner electrode made of a macroporous material,
"material $M_9$" designates an electrically insulating material constituting the colloidal particles of a template used for manufacturing the inner electrode made of a macroporous material. Besides, the terms "material $M_7$" designates a material which is used for stabilizing the structure which is obtained by the process of the invention in which the inner electrode is stabilized together with the outer electrode.

The method of the invention is based on the assembly of inner and outer electrodes which are prepared independently in order to obtain a coaxial electrode architecture.

In contrast to the preparation of both the inner electrode and the outer electrode by potentiostatic electrodeposition of electron conducting or semi-conducting materials through a single colloidal particle template, the process of the invention proposes to manufacture separately the outer electrode and the inner electrode. One template of colloidal particles is used for preparing the outer electrode. The inner electrode is made with another template of colloidal particles, when it is desired that the inner electrode be macroporous. But the inner electrode can also be not macroporous.

Figure 2:
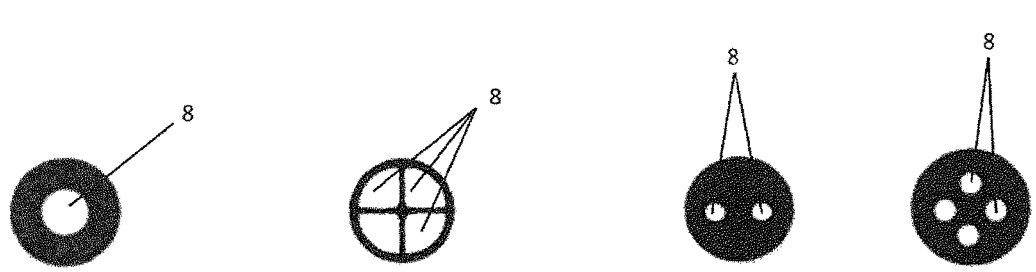
Figure 3:
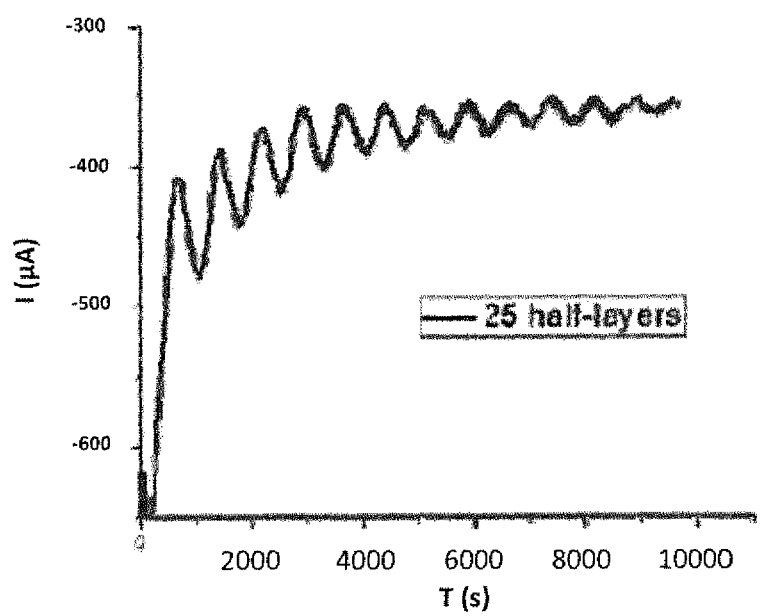
Figure 4:
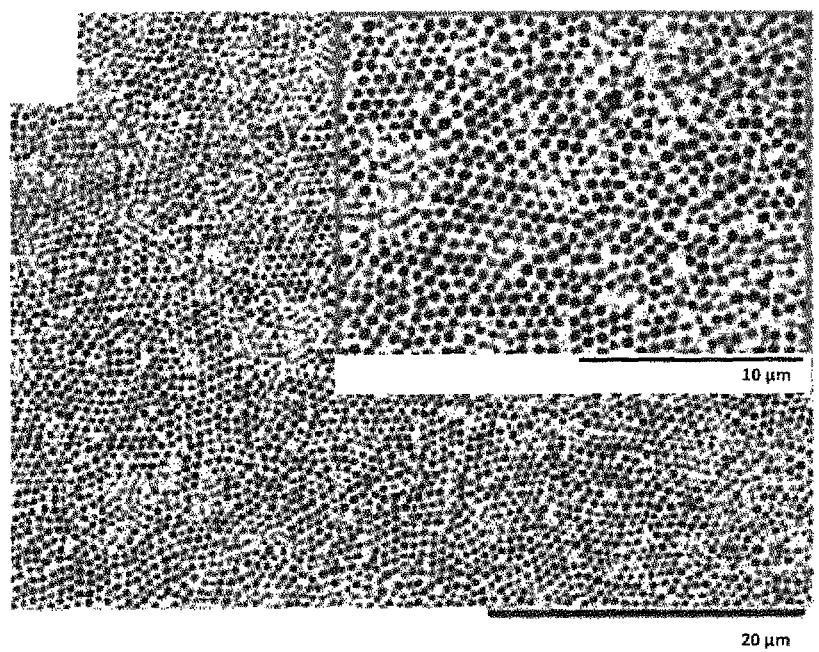
Figure 5:
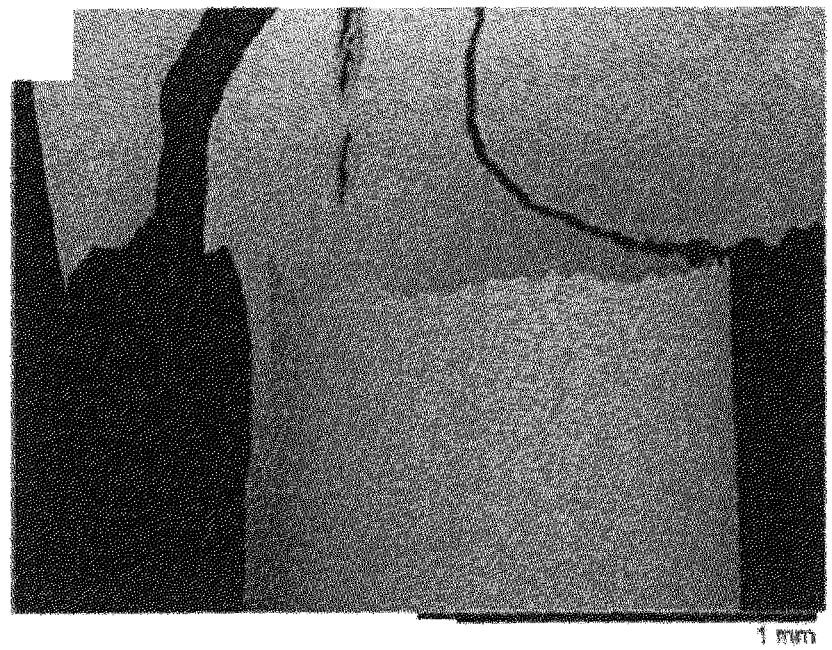
Figure 6:
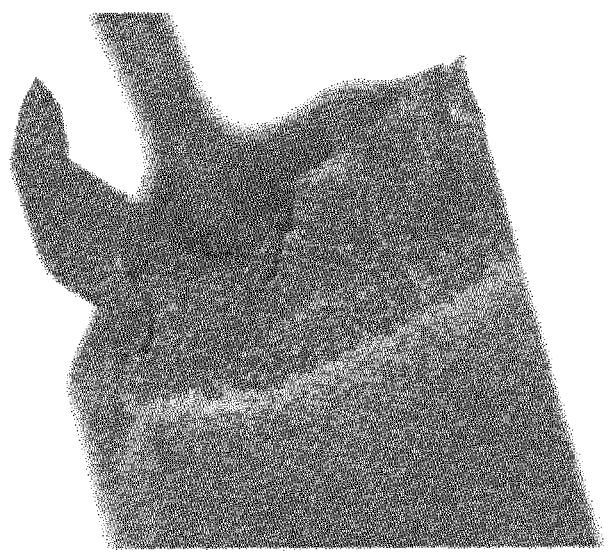
Figure 7:
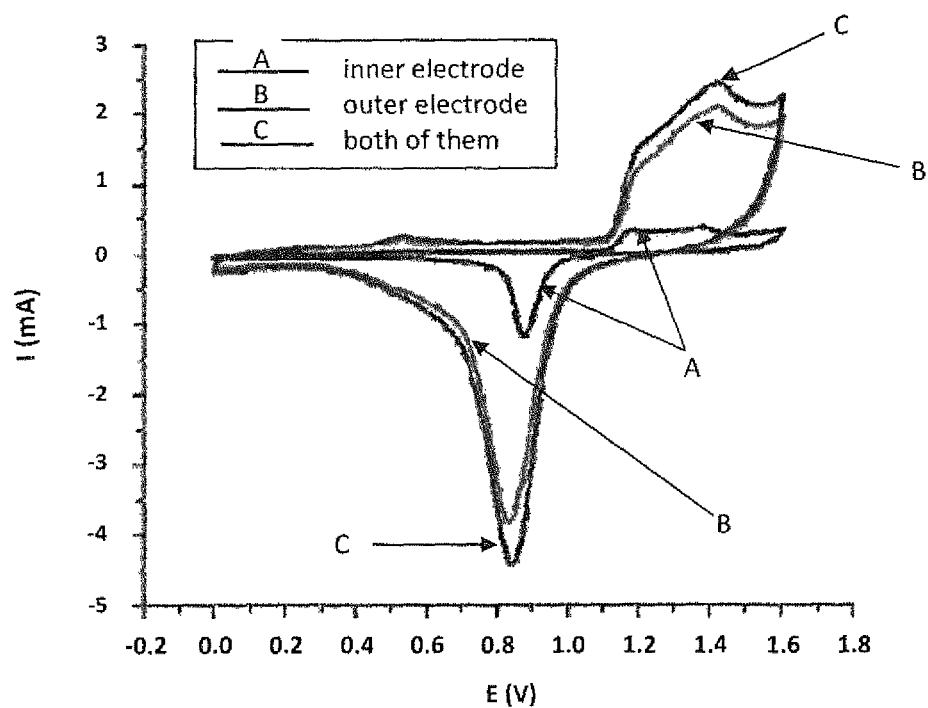
Figure 8:
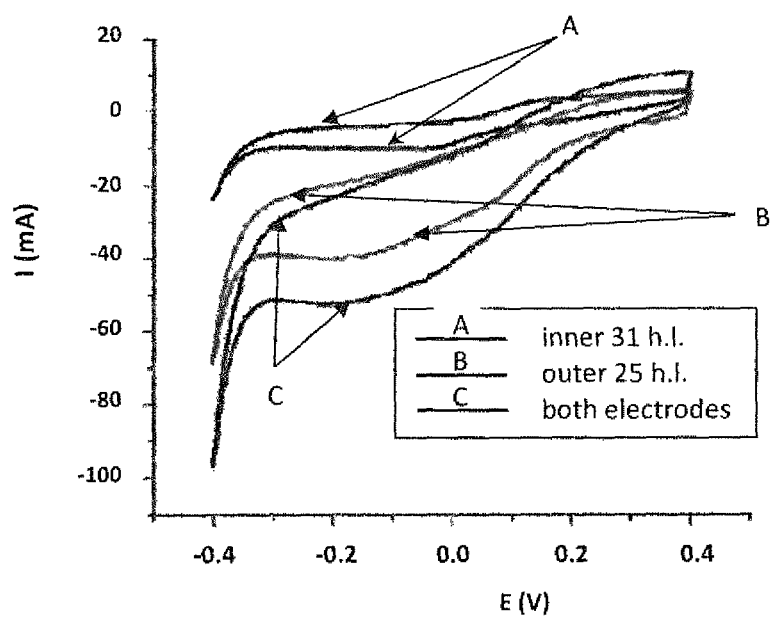

The method for manufacturing a miniaturized cell according to the invention will now be described in reference to the annexed figures in which:

FIG. 1 schematically shows the different steps of the method of the invention, FIG. 2 schematically shows different cross sections of hollow support 4 which can be used for manufacturing the outer electrode, FIG. 3 shows a chronoamperometric curve recorded when carrying out the electrodeposition of gold through the template of colloidal nanoparticles, in example 1, step e) of the process of the invention, FIG. 4 shows a top view image obtained by SEM (Scanning Electron Microscopy), of the structure obtained in step e) of the process of the invention, in example 1, FIG. 5 shows an image obtained by SEM, of the outer electrode obtained in example 1, in step f) but after having removed the glass capillary and the nickel and silver layers, FIG. 6 shows an image obtained by optical microscopy of the assembled inner and outer electrodes obtained in example 1, FIG. 7 shows cyclic voltammograms obtained with the inner electrode alone, the outer electrode alone and the miniaturized cell, obtained in example 1, in 0.5M $H_2SO_4$, FIG. 8 shows cyclic voltammograms obtained with the inner electrode alone, the outer electrode alone and the miniaturized cell, obtained in example 1, during oxygen reduction.

In the method of the invention, the inner electrode and the outer electrode are manufactured independently from each other.

The outer electrode is made of a macroporous electron-conducting or semi-conducting material.

The inner electrode can be made of a macroporous material or of a non macroporous material.

The method for manufacturing the outer electrode, noted 2 in FIG. 1, is as follows.

The first step noted b) in FIG. 1, of the process of manufacture of the outer electrode 2 is to choose a hollow support, noted 4 in FIG. 1, made of an electrically insulating material $M_6$.

This support 4, because hollow, has at least one internal cavity extending along the length of the support and each internal cavity defining a hollow channel.

Each hollow channel is intended to serve as casing for an inner electrode.

This support 4 may be a hollow cylinder having at least one hollow channel, or a hollow parallelepiped having at least one hollow channel. When the support 4 has one internal cavity, it is called "single channel support" and when the support 4 has more than one internal cavity, it is called "multi-channel support". Generally, the support used in the invention has an external diameter of from 100 μm to 1 mm and each channel has an internal diameter of from 10 μm to 500 μm The length of the support used in the invention is generally comprised between 1 mm and 5 cm.

When the support 4 is a parallelepiped, the parallelepiped can have a square section or a rectangular section.

In the same manner, the internal hollow channel(s) may have a circular, square or rectangular section.

FIG. 2 shows cross sections of single channel and multi-channel cylindrical supports which can be used. In FIG. 2, each channel is noted 8.

Because the inner electrode, noted 1 in FIG. 1, will be placed in one internal channel of the support, the dimension of this internal channel must be higher than the external dimension of the inner electrode 1.

The support 4 is intended to be removed at the end of the manufacture of the miniaturized electrode cell according to the invention, this removal leaving a gap between the inner electrode 1 and the outer electrode noted 2 in FIG. 1.

Accordingly, the thickness of the walls of the support 4 must be equal to the width of the gap which is desired between the electrodes 1, 2.

The support 4 can be a capillary made of glass (soda-lime, borosilicate or aluminium silicate), quartz, or a hydrophilic polymer (PMMA).

Preferably, the support 4 is a glass capillary having a total diameter of around 1 mm and an inner diameter of around 300 μm.

The second step, noted c) in FIG. 1, of manufacture of the outer electrode is to deposit on the external surface of the support 4 a layer of an electrically conducting material $M_2$, by an electroless deposition method. Indeed, the support 4 being made of an electrically insulating material, it is necessary to deposit an electrically conducting material by an electroless deposition method in order to be able to then deposit a smoother and thicker layer by an electrodeposition method.

This layer of material $M_2$ is a very thin layer having a thickness (less than 1 μm, and preferably a thickness comprised between 1 nm and 100 nm).

The material $M_2$ can be chosen among Ag, Ni, Cu, Au.

Ag is preferred in the invention, as material $M_2$.

Ag may be deposited by chemical reduction of $[Ag(NH_3)_2]^+$ ions contained in a Tollens' reagent with a glucose solution.

The Tollens' reagent consists of a solution of silver nitrate and ammonia.

Silver is preferred because it forms a "silver mirror" surface on the support 4 which can be used straight-forward as a substrate for the deposition of cylindrical multilayered Langmuir-Blodgett films.

Indeed, the following step, noted d) in FIG. 1, of the method for manufacturing the outer electrode 2, according to the method of the invention, is to deposit on the support 4 coated with the layer of material $M_2$, a template, noted 5 in FIG. 1, of colloidal particles made of an electrically insulating material $M_3$.

The template 5 is formed of a number of layers of colloidal particles which has twice the thickness of the layer of electrically conducting material $M_5$ wanted for forming the outer electrode 2.

Indeed, in this manner, the electro-deposition of the material $M_5$ wanted for forming the outer electrode is homogeneous and there is no risk of overgrowing the template structure.

The template 5 is intended to be removed after the deposit of the material wanted for the outer electrode 2.

The removal of the template 5 of colloidal particles will leave pores in the layer of the material $M_5$ wanted for forming the outer electrode so that an electrode made of a macroporous material $M_5$ is obtained.

After step d) of forming the template 5 of colloidal particles, the next step of the process of the invention is to deposit, through the template 5, a layer of an electrically conducting material $M_4$ on the layer of electrically conducting material $M_2$. This layer is necessary for stabilizing the $M_2$ layer and allows the effective deposition of a smooth $M_5$ layer afterwards. This layer has a thickness of between 1 and 100 nm, preferably 20 nm.

This step is noted e) in FIG. 1.

This step e) enables the homogeneous electro-deposition of the material wanted for forming the outer electrode through the template 5.

The electrically conducting material $M_4$ is chosen among Ni and Cr.

Preferably, when the first layer of electrically conducting material $M_2$ is a layer of Ag, and the second layer of electrically conducting material $M_4$ is a layer of Ni.

The electro-deposition of the material $M_5$ is stopped when the layer L1 has the thickness wanted for the outer electrode 2.

Then, in step noted f) in FIG. 1, the previously cited layer L1 of an electron conducting or semi-conducting material $M_5$ (the material wanted for constituting the outer electrode) is deposited by an electro-deposition method through the template 5.

Then, in step noted g) in FIG. 1, the inner electrode 1 which has been prepared after or before the preparation of the outer electrode, is introduced into the at least one internal hollow channel of the structure obtained in step noted f).

Then, the structure obtained in step g) is stabilized at its two open ends with an electrically insulating material $M_7$, in a step noted h) in FIG. 1.

This material $M_7$ must not be soluble in a solvent in which the materials $M_2$, $M_3$, $M_4$, $M_6$ present at this step as well as, when the inner electrode is made of a macroporous material $M_1$, the material, $M_9$ used for manufacturing such an inner electrode are soluble.

Indeed, the material $M_7$ must remain after the removing of the materials $M_2$, $M_3$, $M_4$, $M_6$ and $M_9$ Indeed, the next step, noted i) in FIG. 1, of the method for manufacturing a miniaturized electrode cell of the invention is to remove the material $M_2$ forming the first layer of electrically conducting material, the material $M_4$ forming the second layer of electrically conducting material and the material $M_6$ forming the support 4.

After this step, a miniaturized electrode cell consisting of two coaxial electrodes and an addressing wire, noted 7 in FIG. 1, is obtained.

The addressing wire 7 is a wire for electrically addressing the electrodes.

But, the miniaturized electrode cell obtained by the method of the invention may consist of more than two electrodes. It can consist of up to 5 coaxial electrodes.

For example, for obtaining a miniaturized electrode cell consisting of three coaxial electrodes, steps b) to g) are repeated before step h) of stabilizing the structure obtained in step g) and before step i) of removing the materials $M_2$, $M_3$, $M_4$ and $M_6$, the inner electrode being in that case, the first structure obtained after step f) of manufacturing a miniaturized electrode cell consisting of two coaxial electrodes.

In the method of the invention, the inner electrode 1 is preferably made of a macroporous material. In this latter case, the inner electrode 1 is preferably prepared by a method comprising the following steps: a1), a2), a3) and a4).

Step a1) is a step of providing a substrate $S_1$ having the shape wanted for the inner electrode 1.

This means that this substrate $S_1$ should be a cylindric substrate, or a parallelepipedic substrate having a square or rectangular section.

The substrate $S_1$ is made of an electron conducting or semi-conducting material $M_8$, preferably the same material as the material $M_1$, wanted for forming the inner electrode 1.

In step a2), a template $T_1$ of colloidal particles made of an electrically insulating material $M_9$ is formed around the outer surface of the substrate $S_1$.

The substrate $S_1$ may be a hollow substrate or a rod of material $M_8$.

Then, in step a3), a layer $L_1$ of an electron conducting or semi-conducting material $M_1$ is deposited on the surface of the substrate $S_1$, by an electro-deposition method, through the colloidal particles of the template $T_1$.

Again, the template $T_1$ has a height which is higher than the wanted thickness of the layer $L_1$.

As for the outer electrode 2, the electro-deposition of the material $M_1$ is stopped when the thickness of the layer $L_1$ plus the thickness of the substrate $S_1$, reach the dimensions wanted for the final inner electrode 1.

Then, the material $M_9$ is removed with a solvent in which the materials $M_1$ and $M_8$ are not soluble.

However, the material $M_9$ can also be eliminated after the inner electrode 1 has been introduced into the internal cavity of the structure obtained in step f) of the preparation of the outer electrode and removed at the same times as the materials $M_2$, $M_3$, $M_4$ and $M_6$ used for preparing the outer electrode 2.

In that case, step i) is a step in which the material $M_9$ forming the template $T_1$ is also removed.

In the method of the invention, the materials $M_1$ and $M_5$, i.e. the materials rendered macroporous which constitute the electrodes of the miniaturized electrode cell of the invention are independently from each other chosen among Pd, Ag, Cr, Au, Pt, Cu, Ni, Zn, an electron-conducting or semi-conducting polymer such as polypyrrole (PPy), polyaniline (PAni), polyacetylene, poly(3,4-ethylenedioxythiophene:sodium poly(styrene sulfonate) (PEDOT:PSS).

Preferably the materials $M_1$, $M_5$ and $M_8$ are Au.

The materials forming the hollow support 4, the template 5 and the template $T_1$, i.e. the materials $M_6$, $M_3$ and $M_9$ are independently from each other chosen among $SiO_2$, a glass or a plastic.

If they are made of plastic they are preferably made of polystyrene.

Step a) of preparation of the inner electrode 1 may be carried out before the first step noted b) of preparation of the outer electrode, or, after the step noted f) of preparation of the outer electrode.

Step h) of stabilizing the structure obtained in step g) is preferably a step of stabilizing the two ends with an epoxy resin or a silicon based adhesive which is liquid at ambient temperature and which is then hardened or reticulated.

When the materials $M_3$ and $M_9$ are $SiO_2$ and the material $M_6$ is a glass which is preferred, and when the material $M_2$ is Ag and the material $M_4$ is Ni, then step i) comprises a step i1) of dissolving the materials $M_3$, $M_6$ and $M_9$ with a solution of hydrofluoric acid, and a step i2) of dissolving the materials $M_2$ and $M_4$ with a solution of nitric acid or of sulfuric acid.

It will clearly appear to the man skilled in the art that when, the support 4 is a multi-channel support, the inner electrodes (macroporous or not) will have to be positioned in each channel.

With the method of the invention, the gap between the electrodes is tunable and can be higher than 100 m.

Thus, the invention also proposes a miniaturized electrode cell consisting of two to 5 coaxial electrodes (1, 2) having a thickness of from 1 to 50 μm made of identical or different conducting or semi-conducting macroporous materials and an addressing wire.

The addressing wire connected to the inner electrode 1 is advantageously the preexisting copper tape that was used to connect the template $T_1$ to the potentiostat during the electro-deposition of the electron-conducting or semi-conducting material $M_1$, during the preparation of the inner electrode.

EXAMPLE 1

Preparation of coaxial double electrode based on glass capillary approach.

In this example, the inner electrode is made of a macroporous material. More precisely, the substrate $S_1$ for preparing the inner electrode is a gold microwire ((d=250 μm) and the support 4 is a Thin Layer Chromatography (TLC) single-channel glass capillary with an outer diameter of 1150 μm and an inner diameter of 280 μm.

1. Preparation of the Samples

Gold microwire (d=250 μm, AlfaAesar, purity 99.9%) has been cut into 3 cm long pieces that are straighten by slight rolling in between two microscope glass slides.

TLC glass capillaries (HIRSCHMANN® LABORGERATE) were cut in 7 cm long pieces.

2. Cleaning and Hydrophilisation of the Samples

In order to clean and hydrophilize the samples, gold microwires were immersed into "Piranha" solution two times for 10 minutes and subsequently rinsed with MilliQ water.

Additionally, cleaned gold microwires were hydrophilized using $UV/O_3$ for 20 min. just before deposition of silica particles (see subsection 4.3).

Prior the "Piranha" treatments, glass capillaries were degreased by 15 min. sonication in chloroform.

"Piranha" solution was prepared by mixing concentrated sulfuric acid (ω=0.98, Sigma Aldrich) with concentrated Hydrogen peroxide (ω=0.3, Sigma Aldrich) in volumetric ratio 75% v/v-25% v/v.

After the cleaning step, samples have been firmly rinsed with MiliQ water and dried with compressed air.

3. Electroless Metallization of Glass Capillaries

The degreased and pre-cleaned glass capillaries have been metallized by a thin silver coating. The metallization is based on the well known reduction of diaminesilver(I) ions by glucose in the presence of anionic surfactant (sodium-dodecyl sulphonate (SDS)).

The composition and the procedure for the preparation of diaminesilver(I) reagent (i.e. Tollens' reagent) is given in Table 1.

TABLE 1

Composition of the solution used for electroless silver metallization of glass capillaries. The components used for the preparation of Tollens' reagent are denoted in blue color.

| Compound | Concentration | Volume/Mass |
| --- | --- | --- |
| Silver-nitrate | 0.1M | 70 ml |
| Sodium-hydroxide | 1M | Added in a drops in silver-nitrate all until the precipitation of $Ag_2O$ was occurring |
| Ammonia | 25% wt. | Added in a drops until the $Ag_2O$ was completely dissolved |
| SDS | Added in a solid state to make the final concentration of 20 mM* | 520 mg |
| Glucose | 20% wt. | 20 ml |

*The first three compounds were mixed as described, and the SDS was added to the pre-measured 70 ml of obtained mixture. After adding SDS mixture was stirred until the SDS was completely dissolved.

The glass capillaries were immersed in Tollens' solution which was pre-heated up to 70° C. In the following step, the glucose solution was added at once and both components were shortly mixed by magnet stirrer.

After the 3 min. metallization was complete and the metalized glass capillaries were firmly rinsed with MilliQ water.

Metallized glass capillaries were used straightforward for the deposition of silica particles by Langmuir-Blodgett technique.

Synthesis and Covalent Modification of Silica Nanoparticles

Silica nanoparticles have been synthesized using well-known Stöber method based on hydrolysis of tetraethyl-orthosilicate (TEOS) in basic solution and polycondensation of the formed silicate acid.

Synthesized silica nanoparticles have been covalently functionalized using a known coupling reaction with 3-aminopropyltriethoxysilane (APTES).

3.1. Synthesis of Silica Nanoparticles

The synthesis of silica beads has been performed in a two-step procedure at room temperature by controlled addition of a TEOS-absolute ethanol mixture (i.e. synthesis mixture), using a single-syringe pump system, into the three-necked flask that contained an absolute ethanol-water-ammonia (ω=0.25) solution (i.e. hydrolyzing solution). Set-up was equipped with stirring system and refrigerant.

First Step—Synthesis of 300 nm Silica "Seeds"

Silica seeds were prepared by adding TEOS directly in the hydrolyzing solution. The experimental conditions are listed in Table 2:

TABLE 2

Experimental condition for the synthesis of 300 nm silica "seeds" (first step).

| Data | Value |
| --- | --- |
| V (TEOS) | 10 ml |
| Hydrolyzing solution: | |
| V (ammonia) | 30 ml |
| V (abs. ethanol) | 200 ml |
| V (water) | 50 ml |
| Speed of the addition of synthesis solution | TEOS was added at once in the hydrolyzing solution |
| Time of synthesis | 2 h 30 min. |
| Speed of mixing | 300 rpm |
| Final diameter of synthesized silica nanoparticles | 300 nm |

Second Step—Synthesis of 600 nm Silica Particles from 300 nm Silica "Seeds"

The pre-synthesized 300 nm silica beads were used as a seeds for the synthesis of 600 nm silica particles (second step). Experimental conditions are shown in Table 3. The excess of ammonia present in the suspension of 300 nm seeds was sufficient enough to hydrolyze the TEOS that has been added in the second step of synthesis.

TABLE 3

Experimental condition for the synthesis of 300 nm silica particles from 300 nm silica "seeds".

| Data | Value |
| --- | --- |
| V (suspension of 300 nm silica beads) | 181 ml |
| Synthesis solution: | |
| V (TEOS) | 45 ml |
| V(abs. ethanol) | 45 ml |
| Hydrolyzing solution: | 181 ml of the suspension of 300 nm silica seeds |
| Speed of the addition of synthesis solution | 8 ml/h |
| Time of synthesis after the synthesis solution was added | 12 h |
| Speed of mixing | 300 rpm |
| Final diameter of synthesized silica particles | 600 nm |

3.2. Covalent Functionalization of Silica Nanoparticles

The surface of silica particles has been covalently modified with APTES.

The amount of added APTES was 10 times larger than the calculated value in order to ensure good surface coverage of the silica beads.

APTES was added into the original post synthetic mixture that contains silica nanoparticles. Mixture was stirred over night and heated next day at 80° C. for 1 h to ensure good covalent binding of APTES.

Calculation of the sufficient amount of APTES (given below) is based on the geometrical consideration that 2 APTES molecules covers 1 $nm^2$ of the surface of silica particles and that density of silica beads is 2.2 $g/cm^3$.

Calculation of the Amount of APTES that has to be Added for the Entire Modification of Silica Particles:

ρ (silica)=2.2 $g/cm^3$ d (one sphere)=292.5 nm

V (one sphere)=$4/3 r^3 \pi$ m (one sphere)=V*ρ

Number of spheres per gram of silica=1 g*1 sphere/m (one sphere)
Area of one sphere=$4r^2\pi$
Surface area per gram of silica spheres=Area of one sphere/Number of spheres per gram of silica
Number of APTES molecules=Surface area per gram of silica spheres*2 molecules
n=N/Na
V(APTES)=n*M(APTES)/ρ(APTES)

3.3. Purification of Covalently Modified Silica Nanoparticles

Functionalized silica nanobeads were purified by rinsing with MilliQ water 10 times. Each rinsing cycle is followed by centrifugation in order to separate the supernatant from the bulk.

Additionally, beads were purified using dialysis against MilliQ water in three separate segments. During the first two dialysis cycles MilliQ water was changed after the 2 h, while for the last one the dialysis was carried-out over night.

4. Fabrication of Colloidal-Crystal Template

Colloidal crystal templates have been prepared using the Langmuir-Blodgett technique based on assembly of covalently functionalized silica nanoparticles.

4.1. Cleaning of Silica Nanoparticles

Silica nanoparticles (d=585 nm), used for the compression of Langmuir-Blodgett films, were previously sonicated for 10 minutes in order to avoid aggregation, washed 5 times with absolute ethanol and centrifuged each time to separate the supernatant from the nanoparticle deposit.

Between two consecutive washing steps, silica nanoparticles were sonicated for a few minutes in order to enhance the efficiency of the washing procedure and disperse them in the bulk.

4.2. Resuspension of Silica Nanoparticles

After completion of washing procedure, silica nanoparticles were redispersed in the ethanol-chloroform mixture (20% v/v-80% v/v respectively). The solvents were added separately. The redespersion of silica beads after adding each solvent was followed by 5 min. of sonication.

Freshly prepared suspensions of silica nanoparticles were immediately used for the preparation of Langmuir-Blodgett films.

4.3. Preparation of Langmuir-Blodgett (LB) Film

The compression of a monolayer of nanoparticles has been carried out on a LB trough (NIMA, type: 622).

The Teflon-coated surface of the apparatus as well as the surface of the moveable barriers was cleaned with dichloromethane.

Apparatus was filled with MilliQ water and dust contaminations were sucked out with a water pump. The suspension of silica nanoparticles was added onto the pre-cleaned water surface drop by drop with an interval of a few seconds between two consecutive adding.

Gold microwires and pre-cleaned silver coated glass capillaries were attached to the dipping mechanism of the LB trough.

TABLE 4

Parameters for the compression of Langmuir-Blodgett film using 600 nm silica beads.

| Parameter | Value |
|---|---|
| Targeted surface tension | 8 mN/m |
| Speed up | 1 mm/min |
| Speed down | 63 mm/min |
| Barrier speed | 29 cm$^2$/min |
| Programmed number of layers | 30 |

5. Fabrication of the Device

The device consists of two cylindrical and macroporous electrodes—the inner (macroporous gold microwire) and outer (mechanically stabilized macroporous film) electrodes. Both electrodes were prepared independently and the final device (which comprises both electrodes) was assembled in the last step of the fabrication.

5.1. Preparation of Inner Electrode

The inner macroporous electrode has been prepared by potentiostatic electrodeposition of gold using a commercially available gold electroplating solution (ECF63, Metalor).

The electrodeposition was performed in a conventional three-electrode system, consisting of working (colloidal-crystal modified gold microwire), reference (Ag/AgCl (3M NaCl)) and cylindrical counter (Pt) electrodes. The gold electrodeposition was performed at the electrode potential of −0.66 V vs Ag/AgCl (3M NaCl).

The length of the colloidal-crystal template immersed into the electroplating solution was dependent on the quality of the template along the wire.

The precise positioning of the sample inside the electrochemical cell has been accomplished by micro-positioning system built on purpose.

5.2. Electrical Addressing of Inner Electrode

The inner electrode was electrically addressed by means of pre-existing copper tape that was used to connect the silica-template covered gold microwire to the potentiostat during the electrodeposition of gold (see subsection 5.1).

5.3. Preparation of Outer Electrode

The colloidal crystal assembled on the surface of the metallized glass capillary, served as a template for the electrodeposition of gold.

Prior to the electrodeposition of gold, the thin silver layer was stabilized by a short (3 min.) potentiostatic electrodeposition of a nickel layer. The nickel layer was electrodeposited using a commercially available nickel electroplating solution (semi-bright nickel solution, AlfaAesar) at −0.9 V vs Ag/AgCl (3M NaCl).

After the electrodeposition of the nickel layer, the gold/silica composite structure was obtained by electrodeposition of gold (ECF63, Metalor) at −0.75 V vs Ag/AgCl (3M NaCl) through the silica based template until the desired number of layers was infiltrated.

As can be seen from FIG. 3, the chromoamperometric curve recorded during this electrodeposition of gold shows well pronounced oscillations which indicate the good quality of the colloidal template and thus the homogeneity of the silver coating underneath. This confirmed by SEM characterization, shown in FIG. 4, where homogeneously distributed pressure observed similar to what was observed in case of the macroporous gold microwire prepared as inner electrode.

5.4. Electrical Addressing of Outer Electrode

The outer electrode was electrically addressed by means of a gold microwire (50 μm). The gold microwire was attached on the surface of outer electrode by a droplet of conductive silver paint (Agar silver paint, Agar). In the following step the structure was heated by an air-gun in order to harden the paint quickly by evaporating the solvent.

5.5. Etching of Silver and Nickel Layers

Silver and nickel layers were removed by etching in 24% wt. nitric-acid (Sigma Aldrich) overnight. This step facilitates the subsequent etching of the glass capillary (see subsection 5.7) since once the underlying silver/nickel layer (that may act as a protective shell) is removed, the glass capillary is easily accessible to hydrofluoric acid.

FIG. 5 shows the topology of the macroporous cylinder obtained at this step, removed from the glass capillary.

5.6. Stabilizing of Assembled Structure

After the inner and the outer electrode were assembled into a device, the whole structure was sealed at its extremities by using the two-component epoxy glue (Quick Set Epoxy Adhesive, RS).

5.7. Etching of Silica Nanoparticles and Glass Capillary

Once the full structure is assembled and the two-component epoxy glue is completely cured, the assembled device is etched with concentrated (48% wt.) HF (Sigma Aldrich) over the 5-6 hours. During the etching, the silica beads were removed in the first few seconds while the etching of the glass capillary required longer time (5-6 h).

The final macroporous coaxial double electrode device was kept in MilliQ water.

FIG. 6 shows the obtained miniaturized cell.

The centrally positioned macroporous gold wire is the inner electrode and the macroporous cylinder is the outer electrode.

The inter-electrode distance is 450 μm.

5.8. Electrochemical Characterization of Coaxial Device

Final confirmation of the structural stability of the coaxial macroporous system with two independently addressable electrodes is obtained by cyclic voltammetry (CV).

CV record was performed using a three electrode system with working electrode (coaxial sample), reference electrode (sat. Ag/AgCl) and counter electrode (Pt cylinder). The experimental conditions are given by Table 5.

TABLE 5

| Parameter | Value |
| --- | --- |
| Scan rate | 100 mV/s |
| Potential window | 0 V to 1.6 V |
| Supporting electrolyte | 0.1M sulphuric acid |
| Deaeration of the electrolyte | Solution was purged with pure argon for 10 min. |

Charge that corresponds to the characteristic cathodic peak (stripping peak) obtained from cyclic voltammograms is directly proportional to the active surface of the electrode.

In case that the formation of short circuits is successfully avoided the calculated charges are different when the two independent coaxial porous electrodes are connected separately. In the control experiment, by connecting the two coaxial porous electrodes together, a cumulative charge for both electrodes is obtained.

The electrode potential is cycled for at least 20 times during the experiment until the current reaches its constant value.

During the measurements the position of the sample is fixed using a micropositioning system built on purpose.

FIG. 7 shows the CV obtained for the inner electrode (curve noted A), the outer electrode (curve noted B), and the miniaturized cell obtained in § 5.7 above (curve noted C), and recorded in 0.5M $H_2SO_4$. Calculated electrode active surface areas for the inner and outer electrode as well as for the short-circuit miniaturized cell are 3.49 $cm^2$ (31 half-layer), 20.77 $cm^2$ (25 half-layer), and 24.56 $cm^2$ respectively.

5.9. Investigation of Electrochemical Functionality of the Device

To investigate the electrochemical functionality of the macroporous coaxial architecture with respect to simple redox couples, cyclic-voltammetry experiments were performed in oxygen saturated sulfuric acid solution. Similar to what was described in subsection 5.8. independently addressable inner and outer macroproous electrodes were connected independently and the cyclic-voltammograms were recorded. The experimental protocol is given by Table 6.

TABLE 6

| Parameter | Value |
| --- | --- |
| Electrolyte | 50 mM sulfuric acid |
| Redox probe | Oxygen dissolved in 50 mM sulfuric acid |
| Scan rate | 5 mV/s |
| Potential window | −0.35 V−+0.4 V |

FIG. 7 shows the obtained cyclic voltamograms. In FIG. 7, curve noted A represents the cyclic voltamogram obtained with the inner electrode connected independently, curve noted B represents the cyclic voltamogram obtained with the outer electrode connected independently and curve noted C represents the cyclic voltamogram obtained with the miniaturized cell obtained in § 5.7 above.

As can be seen from FIG. 8 the individual electrodes exhibit an onset of oxygen reduction current around +0.3 V which is correlated to the respective active surface areas. External short-circuiting of the inner and outer electrode leads to a current which corresponds to the sum of the individual currents.

The invention claimed is:

1. A method for manufacturing a miniaturized electrode cell of coaxial electrodes comprising at least one inner electrode and an outer electrode, the method comprising:
   a) preparing the at least one inner electrode made of an electron conducting or semi-conducting material $M_1$,
   b) providing a hollow support made of an electrically insulating material $M_6$, the support having at least one internal hollow channel, the dimensions of the at least one internal hollow channel being higher than external dimensions of the inner electrode, and thickness of walls of the support being at least equal to width of a gap which is desired between the coaxial electrodes,
   c) depositing on an external surface of the support a layer of an electrically conducting material $M_2$ by an electrodes deposition method,
   d) forming a template of colloidal particles made of an electrically insulating material $M_3$ on the layer of the electrically conducting material $M_2$,
   e) depositing a layer of an electrically conducting material $M_4$ on the layer of the electrically conducting material $M_2$ through the template by an electro-deposition method,
   f) depositing a layer $L_1$ of an electron conducting or semi-conducting material $M_5$ on the layer of the electrically conducting material $M_4$ by an electro-deposition method, through the template to obtain a first structure, the layer $L_1$ having a thickness equal to a thickness of the outer electrode to be obtained, g) introducing the at least one inner electrode into the at least one internal hollow channel of the first structure obtained in f) to obtain a second structure, h) stabilizing the second structure obtained in g) at its two open ends with an electrically insulating material $M_7$ which is not soluble in a solvent in which the materials $M_2$, $M_3$, $M_4$, and $M_6$ are soluble, i) removing the materials $M_2$, $M_3$, $M_4$ and $M_6$, and optionally repeating b) to g) at least one time, the structure obtained after each g) constituting the at least one inner electrode to be introduced into the at least one internal hollow channel of each structure obtained in f).

2. The method according to claim 1, wherein the at least one inner electrode is made of a macroporous electron conducting or semi-conducting material $M_1$ and a) comprises:

a1) providing a substrate $S_1$ having a shape for the inner electrode and made of an electron conducting or semi-conducting material $M_8$, a2) forming a template $T_1$ of colloidal particles made of an electrically insulating material $M_9$, a3) depositing a layer $L_1$ of an electron conducting or semi-conducting material $M_1$ on a surface of the substrate $S_1$ by an electro-deposition method, through the colloidal particles of the template $T_1$, the substrate $S_1$ coated with the layer $L_1$ having, the shape and the external dimensions for the inner electrode, and a4) removing the material $M_9$ with a solvent in which the material $M_1$ is not soluble.

3. The method according to claim 1, wherein the materials $M_1$, $M_5$ and $M_8$ are independently selected from the group consisting of Pd, Ag, Cr, Au, Pt, Cu, Ni, Zn, polypyrrole (PPy), polyaniline (PAni), polyacetylene, and poly(3,4-ethylenedioxythiophene:sodium poly(styrene sulfonate) (PEDOT:PSS).

4. The method according to claim 2, Therein the materials $M_6$, $M_3$ and $M_9$ are independently selected from the group consisting of $SiO_2$, a glass, and a plastic.

5. The method according to claim 1, wherein the materials $M_2$ and $M_4$ are independently selected from the group consisting of Ag, Ni, and Cr.

6. The method according to claim 1, wherein the material $M_2$ is Ag and the material $M_4$ is Ni.

7. The method according to claim 1, wherein a) is carried out after f).

8. The method according to claim 1, wherein h) stabilizes the two open ends of the second structure obtained in g) an epoxy resin or a silicon based adhesive which is then hardened or reticulated.

9. The method according to claim 2, wherein the materials $M_3$ and $M_9$ are $SiO_2$, the material $M_6$ is a glass, the material $M_2$ is Ag, and the material $M_4$ is Ni, and wherein i) comprises:

i1) dissolving the materials $M_3$, $M_6$ and $M_9$ with a solution of hydrofluoric acid, and i2) dissolving the materials $M_2$ and $M_4$ with a solution of nitric acid or sulfuric acid.

10. The method according to claim 2, Therein the support and the substrate $S_1$ are cylinders.

11. The method according to claim 2, wherein the support and the substrate $S_1$ are parallelepipeds with a square or rectangular section.

12. The method according to claim 1, wherein the support is a single channel support.

13. The method according to claim 1, wherein the support is a multi-channel support.

* * * * *